(12) United States Patent
Kim

(10) Patent No.: US 8,545,419 B2
(45) Date of Patent: Oct. 1, 2013

(54) MULTI-FUNCTIONAL COSMETIC DEVICE USING ULTRASONIC WAVE

(75) Inventor: Hyun Jin Kim, Seoul (KR)

(73) Assignee: K.I.C.A. Inc., Seoul (KR)

( * ) Notice: Subject to any disclaimer, the term of this patent is extended or adjusted under 35 U.S.C. 154(b) by 74 days.

(21) Appl. No.: 13/140,337

(22) PCT Filed: Dec. 24, 2009

(86) PCT No.: PCT/KR2009/007785
§ 371 (c)(1),
(2), (4) Date: Jun. 16, 2011

(87) PCT Pub. No.: WO2010/077022
PCT Pub. Date: Jul. 8, 2010

(65) Prior Publication Data
US 2011/0251526 A1 Oct. 13, 2011

(30) Foreign Application Priority Data

Dec. 30, 2008 (KR) .................. 10-2008-0136875
Aug. 28, 2009 (KR) .................. 10-2009-0080164

(51) Int. Cl.
*A61H 1/00* (2006.01)
(52) U.S. Cl.
USPC ............................................. 601/2

(58) Field of Classification Search
USPC .............................................. 601/2
See application file for complete search history.

(56) References Cited

U.S. PATENT DOCUMENTS

| 5,125,423 A | 6/1992 | Butterbrodt | |
|---|---|---|---|
| 2003/0163068 A1* | 8/2003 | Kang | 601/15 |
| 2004/0249320 A1 | 12/2004 | Yamazaki et al. | |
| 2005/0191252 A1* | 9/2005 | Mitsui | 424/62 |
| 2009/0200395 A1* | 8/2009 | Duru et al. | 239/102.1 |

FOREIGN PATENT DOCUMENTS

| JP | 8196965 | * | 8/1996 |
|---|---|---|---|
| KR | 20-0350256 Y1 | | 5/2004 |
| WO | 03015571 A1 | | 2/2003 |
| WO | 2005097350 A1 | | 10/2005 |

OTHER PUBLICATIONS

International Search Report for International Application No. PCT/KR2009/007785 dated Aug. 2, 2010.

* cited by examiner

*Primary Examiner* — Tse Chen
*Assistant Examiner* — Hien Nguyen
(74) *Attorney, Agent, or Firm* — Pearne & Gordon LLP

(57) ABSTRACT

A multi-functional cosmetic device using ultrasonic wave to generate a fine mist of particles that may be ejected from an end of a passage of the nozzle. The cosmetic device is configured to permit ejecting of the fine mist particles even when the device is used upside down so that the user can use the cosmetic device freely at any pose.

9 Claims, 5 Drawing Sheets

MULTI-FUNCTIONAL COSMETIC DEVICE USING ULTRASONIC WAVE

TECHNICAL FIELD

Figure 1:
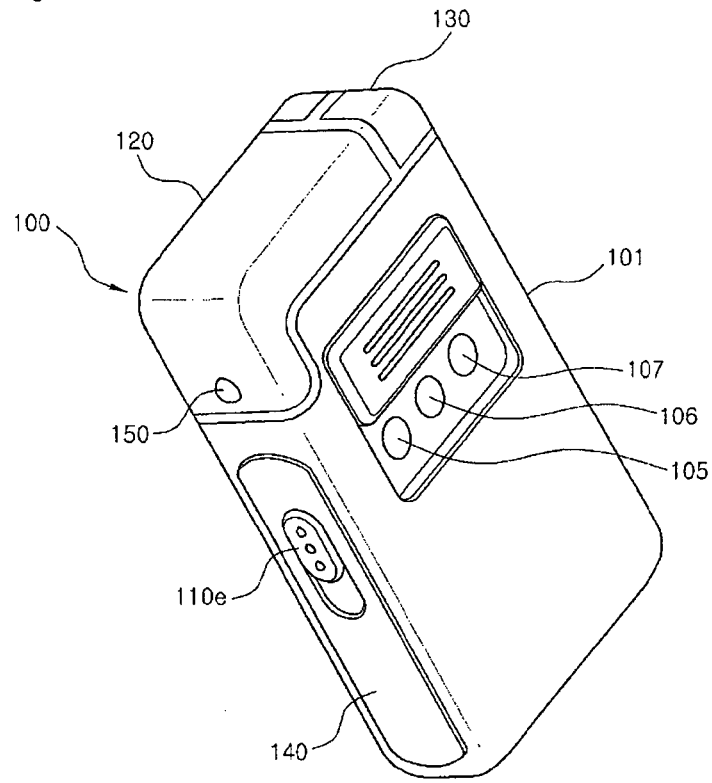

The present invention relates to a multi-functional cosmetic device using ultrasonic wave, and more specifically, to a multi-functional cosmetic device using ultrasonic wave which the user can freely use at any pose and that can provide sufficient cosmetic effects by uniformly spraying mist of beauty water/medicine solution to the face.

BACKGROUND ART

Nowadays, interest in quality life is becoming higher, especially focused on managing physical strength and taking healthy foods. Also, more people, men as well as women, tend to take more interest in treatment of beauty in order to keep their appearance in shape. In this trend, it has become an important point to maintain healthy and beautiful face state. For this purpose, many general cosmetic products such as collagen, nutrition solution and essence are being used for moisturizing, nutrition and enhancing functionality of skin. However, there has been limitation in managing the facial skin through cosmetic products, and the effect of skin protection has been insufficient. The reason is that even the efficient cosmetic product cannot remove the waste material stored in the layer of thick skin due to the thick protein protection layer which is formed below the horny skin layer and isolates the epidermal tissue and the thick skin.

Therefore, various skin caring products are recently being introduced that have the function of regenerating skin cells and making the skin healthy and elastic by promoting the production of collagen and elastic fiber in the thick skin through ultrasonic wave or low frequency current (positive or negative ion current). These products, however, often lack the function of controlling the output of the currents thereby removing the moisture in the skin and causing damage to the skin, and insufficient in providing cosmetic effects because of bad feeling of wearing and the problem of material. Also introduced are cosmetic products for facial skin that generate steam so that skin pores and sweat spots are opened by the steam to remove or absorb secretory or waste material. The skin generating cosmetic products generally have the structure comprising a body having a water-storing vessel in which water is stored, a built-in electric heating panel which is heated by supplied electric power, an outlet path of the steam, and an opening at the upper part that can contact the face. In these steam generating cosmetic devices of the above structure, water in the vessel is heated by the electric heating panel and exited outside the vessel through ventilation hole, thereby applying heated steam to the face to provide moisturizing effect to the skin and improve the health of the skin.

DISCLOSURE OF INVENTION

Technical Problem

These conventional cosmetic devices, however, are difficult to use since the face-contacting portion of the device is looking in the upper direction due to the tendency of the heated steam to float upward, and fixed to the device that the user have to lower his face to contact the steam or the likes. Also, the effect of face caring effect is insufficient due to the difficulty of evenly spraying the steam over the face skin.

In addition, various problems are known including the leak of liquids other than steam from the end of the device and noise generation.

Solution to Problem

The object of the present invention is to solve the above-mentioned problems of prior art cosmetic devices and to provide a multi-functional cosmetic device using ultrasonic wave the user can freely use at any pose and that can provide sufficient cosmetic effects by uniformly spraying mist of beauty water/medicine solution to the face.

Another object of the present invention is to provide a multi-functional cosmetic device that can prevent the leak of liquids other than steam from the end of the device and minimize noise generation.

In order to obtain the objects of the present invention, the multi-functional cosmetic device of the present invention comprises an ultrasonic sprayer which sprays water as fine particles like mist; an ultrasonic massaging unit which massages the face through ultrasonic vibration; a low frequency stimulator which stimulates the surface of skin through electric pulse; an ion function unit which ionizes the nutrition solution through electric pulse so that nutrition can be infiltrated deep inside the skin; a far infrared radiation unit which generates far infrared radiation so that heat can be supplied deep inside the skin; an ultrasonic wave generating unit which generates ultrasonic wave for ultrasonic wave spraying through the ultrasonic sprayer; a low frequency wave/ion generating circuit which generates low frequency wave for low frequency wave stimulation of the skin through the low frequency stimulator and which ionizes the nutrition solution so that nutrition can be infiltrated deep inside the skin; a far infrared radiation driving circuit which supplies energy needed for the far infrared radiation unit to radiate infrared ray; a controller which controls the ultrasonic wave generating unit, the low frequency wave/ion generating circuit and the far infrared radiation driving circuit; and a power supply which supplies power to the ultrasonic wave generating unit, the low frequency wave/ion generating circuit, the far infrared radiation driving circuit and the controller, wherein the ultrasonic sprayer comprises a beauty water/medicine vessel in which at least one of beauty water and medicine is stored for ultrasonic spraying, and an ultrasonic wave spraying nozzle which is mechanically connected to the beauty water/medicine vessel and sprays as mist the solution stored in the beauty water/medicine vessel, and wherein the ultrasonic wave spraying nozzle comprises a nozzle which is installed so that part of the body is inserted into the beauty water/medicine vessel and which ejects the solution in the beauty water/medicine vessel in the form of a particle, an ultrasonic oscillator which is installed at a predetermined location of the body of the nozzle enclosing the body of the nozzle concentrically with the concentric axis being the longitudinal axis of the body of the nozzle and which, by ultrasonic oscillation, lets the solution in the beauty water/medicine vessel get ejected through the nozzle in the form of a particle, and a mesh which is installed at the upper end of the nozzle and which makes the particles of the solution ejected from the upper end of the nozzle to finer particles by passing the particles through the mesh structure, and wherein a side hole is formed around the upper end of the nozzle inserted into the beauty water/medicine vessel so that the solution can be supplied from the beauty water/medicine vessel to the nozzle even when the beauty water/medicine vessel is used upside down.

The beauty water/medicine vessel is preferably formed with a double vessel structure consisting of an outer vessel which constitutes the overall appearance of the vessel, and an internal vessel which is formed inside the outer vessel in one body with the outer vessel through a common partition wall. And at least one through hole is formed on the wall of the inner vessel for connecting with the outer vessel.

Also, preferably, a water-proofing nozzle silicon is installed on the inlet of the inner vessel of the beauty water/medicine vessel in order to enhance the sealing of the inner vessel by surrounding the body of the nozzle and to enhance the effect of preventing the solution inside the inner vessel from leaking outside of the vessel even when the beauty water/medicine vessel becomes upside down.

Also, preferably, a fine through hole is formed on the upper surface of the water-proofing nozzle silicon inserted into the nozzle in order to keep the solution ejecting out of the vessel even when inside of the vessel approaches a vacuum due to continuous consumption of the solution inside the inner vessel of the beauty water/medicine vessel.

A wave spring is further installed on the upper surface of the mesh in order to prevent leaking of water from the end of the nozzle by maintaining the mesh at a constant pressure against the nozzle, and wherein flat washers are installed between the wave spring and the mesh, and between the mesh and the upper end of the nozzle respectively for lessening vibration and protecting the upper and lower surfaces of the mesh.

The wave spring, the mesh and the flat washers are installed with a layered structure in the order of the first flat washer, the mesh, the second washer, and the wave spring from bottom to top inside the upper cap combined to the upper portion of the nozzle.

Also, preferably, a silicon cap is further installed between the upper cap and the upper portion of the nozzle with contacted to the nozzle, in order to reduce noise due to the oscillation of the ultrasonic oscillator and to prevent leaking of liquid other than the spray from the upper end of the nozzle.

Also, preferably, a lower cap is further installed on the upper portion of the nozzle enclosing the lower portion of the upper cap in order to secure the connection of the upper cap and the upper portion of the nozzle and to prevent leaking of liquid other than the spray from the upper end of the nozzle together with the silicon cap.

Also, preferably, a high voltage circuit can be further included between the controller and the ultrasonic sprayer in order to apply high voltage between the ultrasonic sprayer and the user so that the fine liquid particle sprayed from the ultrasonic sprayer is charged and decomposed into finer particles and makes the fine liquid particles sprayed from the ultrasonic sprayer to be penetrated more deep inside the skin of the user.

Advantageous Effects of Invention

By using the multi-functional cosmetic device using ultrasonic wave according to the present invention, the user can use the cosmetic device freely at any pose since a fine through hole is formed on the upper surface of the nozzle portion in order to keep the solution ejecting out of the vessel and spraying mist of the water/medicine solution even when the device is used upside down.

BRIEF DESCRIPTION OF DRAWINGS

FIG. 1 shows the outer appearance of the multi-functional cosmetic device using ultrasonic wave according to the present invention.

FIG. 2 illustrates the state where the spraying nozzle and beauty water/medicine vessel are installed to the multi-functional cosmetic device using ultrasonic wave according to the present invention.

FIG. 3 shows the overall system configuration of the multi-functional cosmetic device using ultrasonic wave according to the present invention.

FIG. 4 illustrates the appearance of the multi-functional cosmetic device using ultrasonic wave according to the present invention in which the ultrasonic wave spraying nozzle and the beauty water/medicine vessel are combined.

FIG. 5 shows the inner structure of each component of the multi-functional cosmetic device using ultrasonic wave according to the present invention in which the ultrasonic wave spraying nozzle and the beauty water/medicine vessel are combined.

FIG. 6 shows the structure of the beauty water/medicine vessel of the multi-functional cosmetic device using ultrasonic wave according to the present invention.

FIG. 7 shows the combining structure of the upper part of the nozzle and the lower and upper cap of the multi-functional cosmetic device using ultrasonic wave according to the present invention.

FIG. 8 shows the overall system configuration of another embodiment of the multi-functional cosmetic device using ultrasonic wave according to the present invention.

FIG. 9 illustrates the embodiment of the multi-functional cosmetic device using ultrasonic wave according to the present invention in which the solution inlet of the lower end of the nozzle is formed in the structure of a cone with its diameter decreasing from outside to inside.

DESCRIPTION ON THE NUMERALS IN THE DRAWINGS

105. ultrasonic spray/massage function selection switch
106. low frequency stimulation/ion function selection switch
107. far infrared radiation function selection switch
110. ultrasonic sprayer
**110*e***. spraying hole
111. beauty water/medicine vessel
**111*a*, 111*b***. external, internal vessel
**111*h***. penetration hole
112. water-proofing nozzle silicon
113. cap of beauty water/medicine vessel
114. ultrasonic wave spraying nozzle
115. nozzle
**115*e***. solution inlet
**115*h***. side hole
116. ultrasonic oscillator
**116*t***. oscillator terminal
117. mesh
118. wave spring
**119*a*, 119*b***. First, second flat washer
120. ultrasonic massaging unit
130. low frequency stimulator
140. ion function unit
150. far infrared radiator
160. ultrasonic wave generating circuit
170. low frequency wave/ion generating circuit
180. far infrared radiation driving circuit
190. controller
200. power supply
210. battery
220. DC/DC converter
230. high voltage circuit 310. fixing nut of nozzle
320. combining nut of beauty water/medicine vessel
510. upper cap
520. silicon cap
530. lower cap

MODE FOR THE INVENTION

The example of the present invention will be described in detail with reference to the drawings attached.

Figure 2:
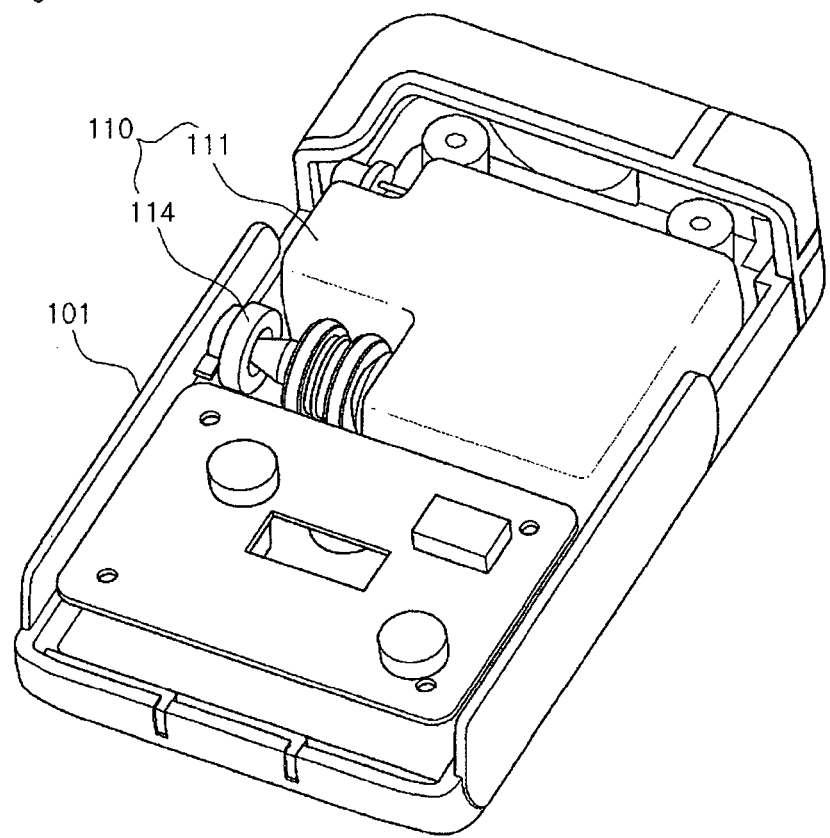
Figure 3:
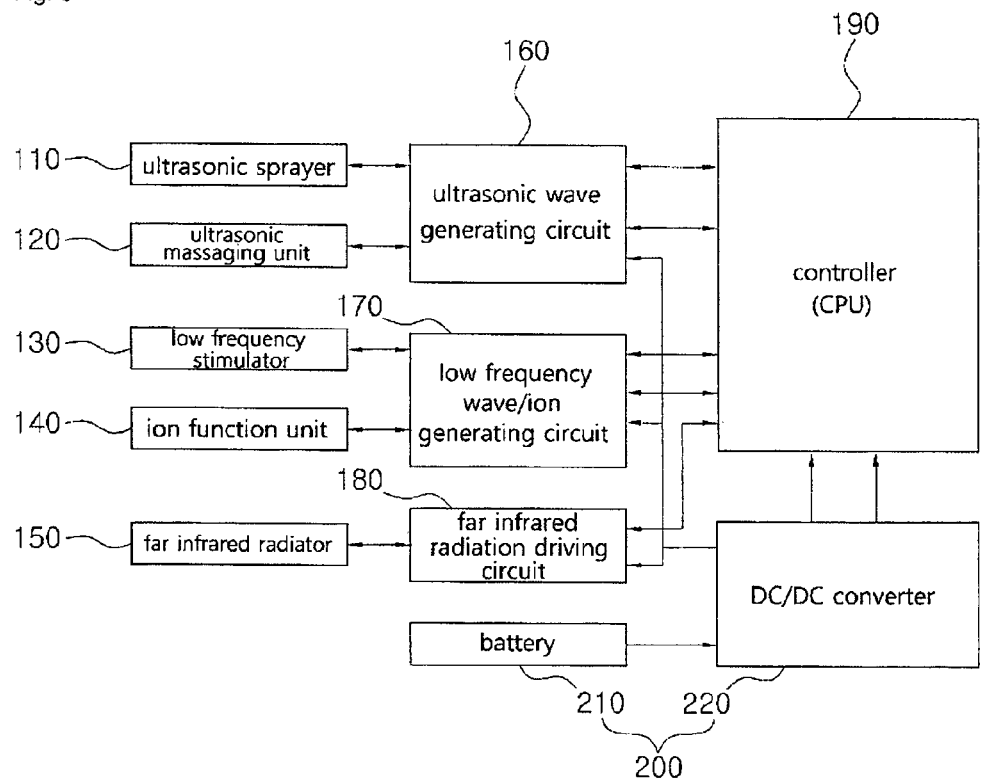

FIGS. 1-3 show the multi-functional cosmetic device using ultrasonic wave according to the present invention, FIG. 1 showing the outer appearance, FIG. 2 the spraying nozzle and beauty water/medicine vessel, and FIG. 3 the overall system configuration.

Referring to FIGS. 1-3, the multi-functional cosmetic device 100 using ultrasonic wave according to the present invention comprises an ultrasonic sprayer 110, an ultrasonic massaging unit 120, a low frequency stimulator 130, an ion function unit 140, a far infrared radiation unit 150, an ultrasonic wave generating unit 160, a low frequency wave/ion generating circuit 170, a far infrared radiation driving circuit 180, a controller 190, and a power supply 200.

The ultrasonic sprayer 110 sprays water as fine particles like mist.

The ultrasonic massaging unit 120 massages the face through ultrasonic vibration.

The low frequency stimulator 130 stimulates the surface of skin through electric pulse.

The ion function unit 140 ionizes the nutrition solution through electric pulse so that nutrition can be infiltrated deep inside the skin.

The far infrared radiation unit 150 radiates far infrared ray so that heat can be supplied deep inside the skin.

The ultrasonic wave generating unit 160 generates ultrasonic wave for ultrasonic wave spraying through the ultrasonic sprayer 110. The ultrasonic wave generating unit 160 comprises as a constituent an ultrasonic generator 116 which will be described later.

The low frequency wave/ion generating circuit 170 generates low frequency wave for low frequency wave stimulation of the skin through the low frequency stimulator 130, and ionizes the nutrition solution so that nutrition can be infiltrated deep inside the skin.

The far infrared radiation driving circuit 180 supplies energy needed for the far infrared radiation unit 150 to radiate infrared ray.

The controller 190 controls the ultrasonic wave generating unit 160, the low frequency wave/ion generating circuit 170 and the far infrared radiation driving circuit 180. CPU can be used as the controller 190.

The power supply 200 supplies power to the ultrasonic wave generating unit 160, the low frequency wave/ion generating circuit 170, the far infrared radiation driving circuit 180 and the controller 190. The power supply 200 can comprise a battery 210 supplying direct current, and a DC/DC converter 220 which converts the low voltage power provided by the battery 210 to a high voltage power for driving the circuits and supplies the power to the circuits.

In FIG. 1, the numeral 101 denotes external case, 105 the ultrasonic spray/massage function selection switch, 106 the low frequency stimulation/ion function selection switch, 107 the far infrared radiation function selection switch, and 110e the spraying hole through which the mist of the beauty water/medicine solution that is sprayed by the upper end of an ultrasonic wave spraying nozzle 114 of a ultrasonic sprayer 110, which will be described later, is ejected to outside. The present invention illustrates the case where a cover is installed so that the spraying hole can by opened or closed.

Figure 4:
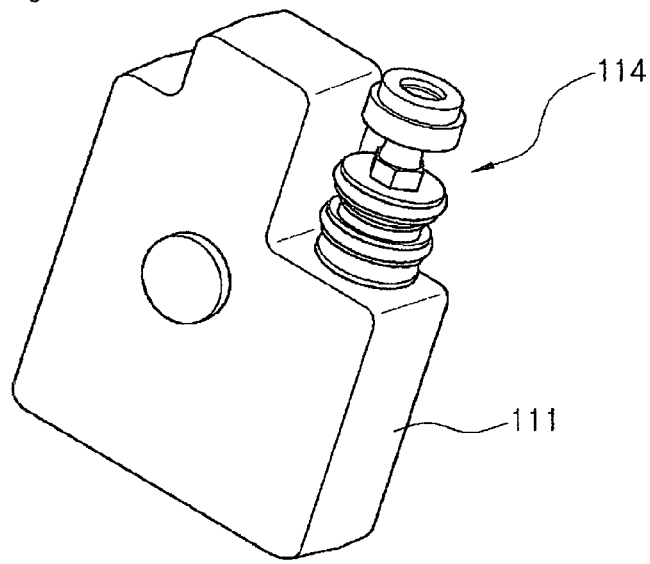

The ultrasonic sprayer 110, as shown in FIG. 4, comprises a beauty water/medicine vessel 111 in which at least one of beauty water and medicine is stored for ultrasonic spraying, and an ultrasonic wave spraying nozzle 114 which is mechanically connected to the beauty water/medicine vessel 111 and sprays as mist the solution stored in the beauty water/medicine vessel 111.

Figure 5:
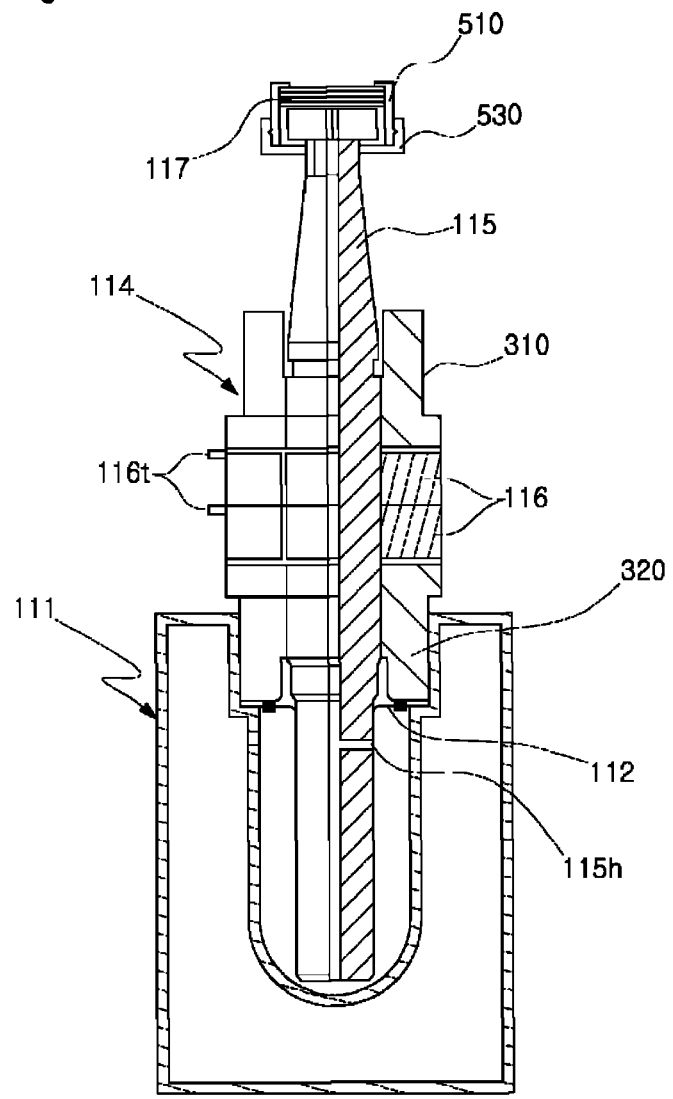

The ultrasonic wave spraying nozzle 114, as shown in FIG. 5, comprises a nozzle 115 which is installed so that part of the body is inserted into the beauty water/medicine vessel 111 and which ejects the solution in the beauty water/medicine vessel 111 in the form of a particle, an ultrasonic oscillator 116 which is installed at a predetermined location of the body of the nozzle 115 enclosing the body of the nozzle concentrically with the concentric axis being the longitudinal axis of the body of the nozzle 115 and which, by ultrasonic oscillation, lets the solution in the beauty water/medicine vessel 111 get ejected through the nozzle 115 in the form of a particle, and a mesh 117 which is installed at the upper end of the nozzle 115 and which makes the particles of the solution ejected from the upper end of the nozzle 115 to finer particles by passing the particles through the mesh structure. In FIG. 5, the numeral 116t is an oscillator terminal for connecting to the power supplying line to the ultrasonic oscillator 116, 310 a fixing nut of nozzle and 320 a combining nut of beauty water/medicine vessel.

Side hole 115h is installed around the upper end of the nozzle inserted into the beauty water/medicine vessel 111 so that solution can be supplied from the beauty water/medicine vessel 111 to the nozzle 115 when the beauty water/medicine vessel 111 is used upside down (in other words, when the user uses the cosmetic device of the present invention upside down).

Figure 6:
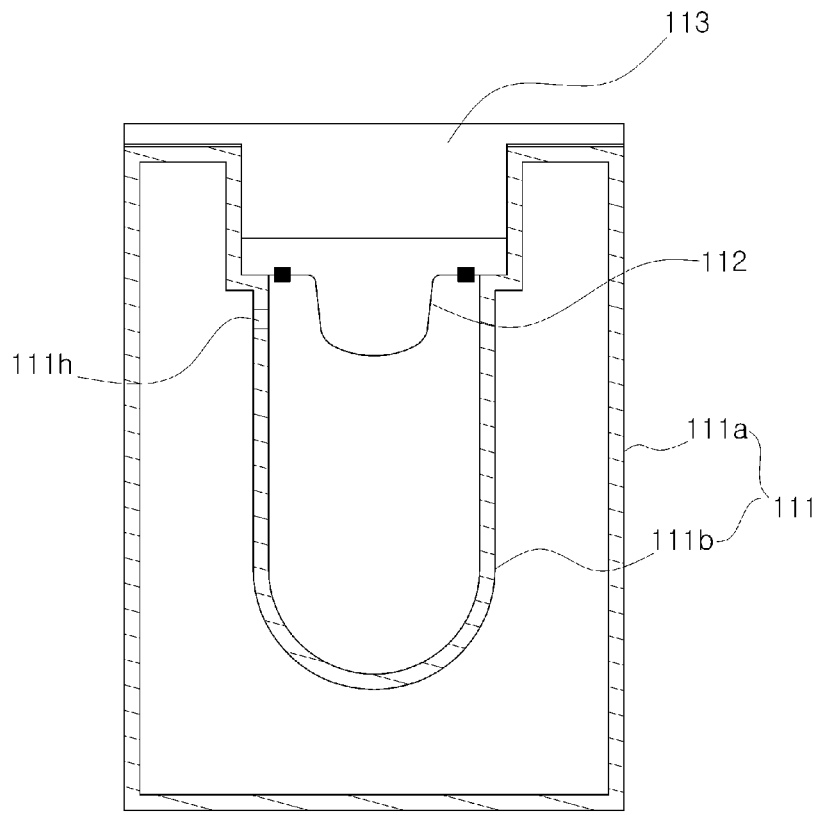

The beauty water/medicine vessel 111, as shown in FIG. 6, is formed with a double vessel structure consisted of an outer vessel 111a which constitutes the overall appearance of the vessel, and an internal vessel 111b which is formed inside the outer vessel 111a in one body with the outer vessel 111a through a common partition wall. And at least one through hole 111h is formed on the surface of the inner vessel 111b for connecting with the outer vessel 111a.

Also, preferably, a water-proofing nozzle silicon 112 is installed on the inlet of the inner vessel 111b of the beauty water/medicine vessel 111 in order to enhance sealing the inner vessel 111b by surrounding the body of the nozzle and to enhance the effect of preventing the solution inside the inner vessel 111b from leaking outside of the vessel when the beauty water/medicine vessel 111 becomes upside down.

Also, preferably, fine through hole (not shown) is formed on the upper surface of the water-proofing nozzle silicon 112 inserted into the nozzle 115 in order to keep the solution ejecting out of the vessel even when inside of the vessel approaches a vacuum due to continuous use of the solution inside the inner vessel 111b of the beauty water/medicine vessel 111. In FIG. 6, the numeral 113 designates a cap of beauty water/medicine vessel. The beauty water/medicine vessel 111 can be treated or sold separately with beauty water or medicine filled in it and the cap closed. The beauty water/medicine vessel 111 with the cap closed can be easily connected to the ultrasonic wave spraying nozzle 114 by opening the cap 113 of the beauty water/medicine vessel and inserting the lower part of the ultrasonic wave spraying nozzle 114 into the inner vessel 111b of the beauty water/medicine vessel 111.

Figure 7:
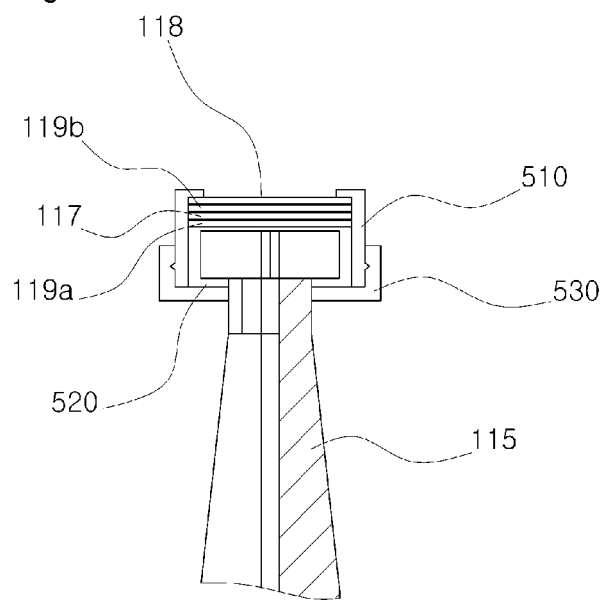

Also, preferably, as shown in FIG. 7, a wave spring 118 is installed on the upper surface of the mesh 117 in order to prevent leaking of water from the end of the nozzle 115 by maintaining the mesh 117 at a constant pressure against the nozzle 115, and flat washers 119a, 119b are installed between the wave spring 118 and mesh 117, and between the mesh 117 and the upper end of the nozzle 115 respectively for lessening vibration and protecting the upper and lower surfaces of the mesh 117.

Also, preferably, the wave spring 118, the mesh 117 and the flat washers 119a, 119b are installed with a layered structure in the order of the first flat washer 119a, the mesh 117, the second washer 119b, and the wave spring 118 from bottom to top inside the upper cap 510 combined to the upper portion of the nozzle 115.

Also, preferably, a silicon cap 520 is further installed contacting the nozzle 115 between the upper cap 510 and the upper portion of the nozzle 115 in order to reduce noise due to the oscillation of the ultrasonic oscillator 116 and to prevent leaking of liquid other than the spray from the upper end of the nozzle 115.

And, preferably, a lower cap 530 is further installed on the upper portion of the nozzle 115 enclosing the lower portion of the upper cap 510 in order to secure the connection of the upper cap 510 and the nozzle 115 and to prevent leaking of liquid other than the spray from the upper end of the nozzle 115.

Figure 8:
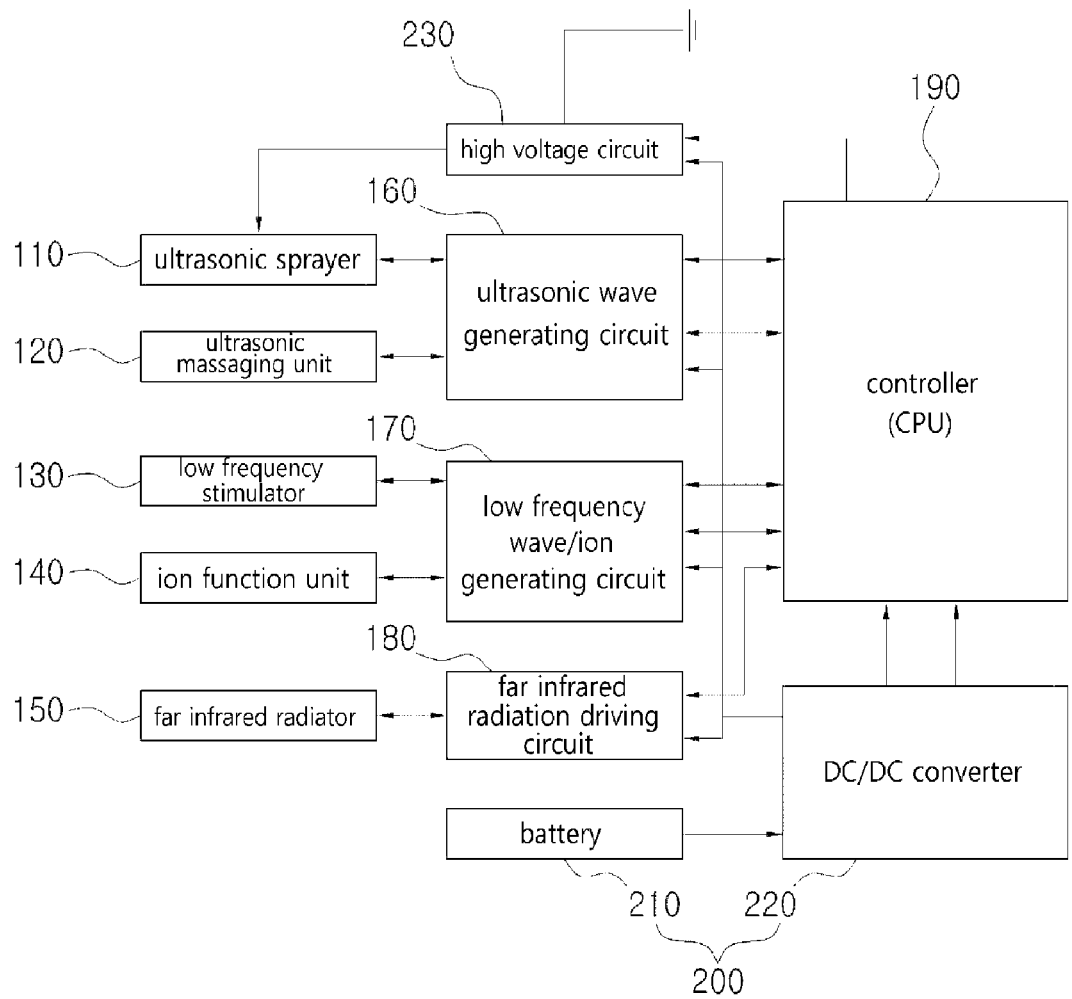

Also, preferably, as shown in FIG. 8, a high voltage circuit 230 can be included between the controller 190 and the ultrasonic sprayer 110 in order to introduce high voltage (for example, 12 kV) between the ultrasonic sprayer 110 and the user so that the fine liquid particle sprayed from the ultrasonic sprayer 110 is charged and decomposed into finer particles and makes the fine liquid particles sprayed from the ultrasonic sprayer 110 more penetrable deep inside the skin of the user.

Figure 9:
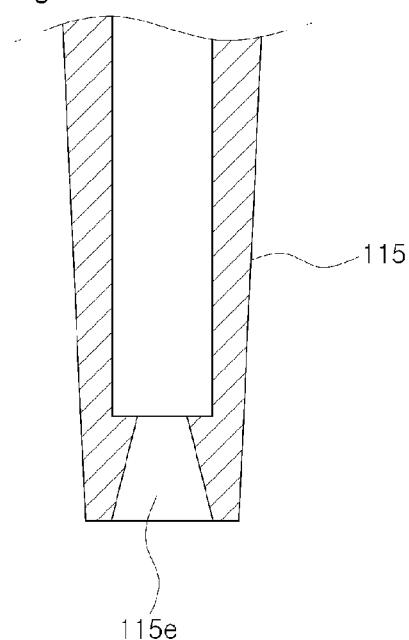

Also, preferably, as shown in FIG. 9, the solution inlet 115e of the lower end of the nozzle 115 is formed in the structure of a cone with its diameter decreasing from outside to inside. By using this structure, the solution in the beauty water/medicine vessel 111, while the solution stored in the beauty water/medicine vessel 111 is introduced into the internal pipe of the nozzle 115 through the solution inlet 115e at the lower end of the nozzle 115 by the ultrasonic oscillation of the ultrasonic oscillator 116, can easily enter inside the nozzle 115, and once the solution has entered the nozzle 115, the solution cannot easily go out of the nozzle 115. In the end, by this structure, the solution in the beauty water/medicine vessel 111 is easily raised from the solution inlet 115e at the lower end of the nozzle 115 to the outlet at the upper end of the nozzle 115.

Meanwhile, the appearance of the lower portion of the nozzle 115 shown in FIG. 9 is different from the appearance of the lower portion of the nozzle 115 shown in FIG. 5, illustrating that the nozzle 115 can be designed in the form as shown in FIG. 5 or as shown in FIG. 9.

Then, the operation of the multi-functional cosmetic device according to the present invention having the above described structure will be briefly described.

When the power switch of the cosmetic device of the present invention is turned on by the user, operating power is supplied from the power supply 200 to the ultrasonic wave generating circuit 160, the low frequency wave/ion generating circuit 170, the far infrared radiation driving circuit 180, and the controller 190, setting each circuit at stand-by state. At this state, if any function selection switch, the ultrasonic spray/massage function selection switch 105, for example, is selected, the controller 190 sends a command to drive to the ultrasonic wave generating circuit 160, driving the ultrasonic wave generating circuit 160 and generating ultrasonic wave. The generated ultrasonic wave is transmitted to the nozzle 115, thereby oscillating the nozzle 115 and mesh 117 at the upper end of the nozzle through the ultrasonic wave. As the nozzle 115 oscillates, the solution in the beauty water/medicine vessel 111 is turned into fine particles, moves to the upper end of the nozzle through the pipe in the nozzle 115 and, when the particles of the solution reaches the mesh 117, the particles are transformed into smaller particles according to the mesh size of the mesh 117 and sprayed like mist into the air. Therefore, when the mist is applied to the face or certain part of the body, water is supplied to the part and the part is moisturized. At this step, in another embodiment of the present invention as shown in FIG. 8, high voltage circuit 230 is operated introducing high voltage between the ultrasonic sprayer 110 and the user. In other words, the fine particles (mist) sprayed from the ultrasonic sprayer 110 are charged with high voltage negative charge and the user is charged with grounded positive charge. Then, attracting force is generated between the two charged objects, and the larger the introduced voltage is, the greater the attracting force becomes thereby making the mist decomposed into smaller particles (for example, 3-10 m) and well attached to the skin of the user. Also, the medicine or nutrient is uniformly deposited on the skin or face by the spraying through introduction of high voltage. It also has the advantage of excellent spraying effect at the edge of the spray hole. And, the mist is absorbed deep inside the skin since the particles and skin are charged each other. Also, uniform spraying saves the amount of medicine required for spraying.

Meanwhile, while spraying the ultrasonic wave, massaging effect by ultrasonic wave can be obtained by lightly rubbing the ultrasonic massaging unit 120 in contact with the face or certain part of the body.

The case where the ultrasonic spray/massage function selection switch has been selected has been described so far, but even when other function selection switch such as low frequency stimulation/ion function selection switch 106 or far infrared radiation function selection switch 107 is selected, each corresponding circuit is driven by the command from the controller 190 and performs its function as in the case of the ultrasonic wave generating circuit 160. When the low frequency stimulation/ion function selection switch 106 is selected by the user, for example, the low frequency wave/ion generating circuit 170 is driven to generate low frequency wave and ion so that the user can get the effect of low frequency wave stimulation by contacting the low frequency stimulator 130 to the face or certain part of the body, and can contact the ionized mist through the spraying hole 110e. Also, when the far infrared radiation function selection switch 107 is selected by the user, the far infrared radiation driving circuit 180 is driven and far infrared rays are radiated through the far infrared radiator 150. In this way, far infrared radiation is applied to the face or a certain area of a body supplying heat deep inside the skin.

The above described three function selection switches (although the case with three function selection switches is illustrated in this example, 4 or 5 function selection switches can be also installed) can be selected all at once, or one or two at a time. When all the function selection switches (105, 106, 107) are selected, obviously all the functions corresponding each function selection switch operate and various functions are available to the user at the same time.

Meanwhile, if the user uses the cosmetic device of the present invention upside down while using the device in various ways (i.e. when the beauty water/medicine vessel 111 is used in a state upside down), as described above, side hole 115h is installed around the upper end of the nozzle inserted into the beauty water/medicine vessel 111 (more precisely, the internal vessel 111b) so that solution can be supplied from the beauty water/medicine vessel 111 to the nozzle 115 through the side hole 115h. Therefore, it is possible to use the cosmetic device of the present invention freely at any pose since the mist of the beauty water/medicine is constantly sprayed from the end of the nozzle 115.

The invention has been described with reference to preferable examples, but the invention is not limited by the examples which can obviously be modified and specified within the scope of the present invention. Therefore, the scope of the invention should be interpreted in terms of the claims and any technical idea which is equivalent to the present invention is deemed to be within the scope of the invention.

The invention claimed is:

1. A multi-functional cosmetic device, comprising:
   an ultrasonic sprayer which sprays water as fine particles like mist,
   an ultrasonic massaging unit which massages the face through ultrasonic vibration,
   a low frequency stimulator which stimulates the surface of skin through electric pulse,
   an ion function unit which ionizes a nutrition solution through electric pulse so that nutrition can be infiltrated deep inside the skin,
   a far infrared radiation unit which generates far infrared radiation so that heat can be supplied deep inside the skin,
   an ultrasonic wave generating unit which generates ultrasonic wave for ultrasonic wave spraying through the ultrasonic sprayer,
   a low frequency generating circuit which generates low frequency wave for low frequency wave stimulation of the skin through the low frequency stimulator and which ionizes the nutrition solution so that nutrition can be infiltrated deep inside the skin,
   a far infrared radiation driving circuit which supplies energy needed for the far infrared radiation unit to radiate infrared ray,
   a controller which controls the ultrasonic wave generating unit, the low frequency generating circuit and the far infrared radiation driving circuit, and
   a power supply which supplies power to the ultrasonic wave generating unit, the low frequency generating circuit, the far infrared radiation driving circuit and the controller,
   wherein the ultrasonic sprayer comprises:
   a beauty vessel in which at least one of beauty water and medicine is stored for ultrasonic spraying,
   an ultrasonic wave spraying nozzle which is mechanically connected to the beauty vessel, wherein the spraying nozzle includes an internal passage in fluid communication with the beauty vessel and the internal passage including an end configured to spray the solution stored in the beauty vessel as a mist of particles, and wherein the ultrasonic wave spraying nozzle comprises a nozzle which is installed so that part of the body is inserted into the beauty vessel and which ejects the solution in the beauty vessel as the mist of particles,
   an ultrasonic oscillator which is installed at a predetermined location of the body of the nozzle enclosing the body of the nozzle concentrically with the concentric axis being the longitudinal axis of the body of the nozzle and which, by ultrasonic oscillation, lets the solution in the beauty vessel get ejected through the end of the internal passage of the nozzle as the mist of particles,
   a mesh which is installed at the upper end of the nozzle and covering the end of the internal passage of the nozzle, wherein the particles of the mist being ejected through the end of the internal passage are made finer by passing through the mesh, wherein a wave spring is further installed on the upper surface of the mesh in order to prevent leaking of water from the end of the nozzle by maintaining the mesh at a constant pressure against the nozzle, and wherein flat washers are installed between the wave spring and the mesh, and between the mesh and the upper end of the nozzle respectively for lessening vibration and protecting the upper and lower surfaces of the mesh,
   a side hole in fluid communication with the passage of the nozzle, wherein the side hole is inserted into the beauty vessel so that the solution can be supplied from the beauty vessel to the nozzle even when the beauty vessel is used upside down, and
   a high voltage circuit included between the controller and the ultrasonic sprayer in order to apply high voltage between the ultrasonic sprayer and a user so that the fine liquid particle sprayed from the ultrasonic sprayer is charged and decomposed into finer particles and makes the fine liquid particles sprayed from the ultrasonic sprayer to be penetrated more deep inside the skin of the user.

2. The multi-functional cosmetic device of claim 1, wherein the beauty vessel is formed with a double vessel structure consisting of an outer vessel which constitutes the overall appearance of the vessel, and an internal vessel which is formed inside the outer vessel in one body with the outer vessel through a common partition wall.

3. The multi-functional cosmetic device of claim 2, wherein at least one through hole is formed on the wall of the inner vessel for connecting with the outer vessel.

4. The multi-functional cosmetic device of claim 2, wherein a water-proofing nozzle silicon is installed on the inlet of the inner vessel of the beauty vessel in order to enhance the sealing of the inner vessel by surrounding the body of the nozzle and to enhance the effect of preventing the solution inside the inner vessel from leaking outside of the vessel even when the beauty vessel becomes upside down.

5. The multi-functional cosmetic device of claim 4, wherein a fine through hole is formed on the upper surface of the water-proofing nozzle silicon inserted into the nozzle in order to keep the solution ejecting out of the vessel even when inside of the vessel approaches a vacuum due to continuous consumption of the solution inside the inner vessel of the beauty vessel.

6. The multi-functional cosmetic device of claim 1, wherein the wave spring, the mesh and the flat washers are installed with a layered structure in the order of the first flat washer, the mesh, the second washer, and the wave spring from bottom to top inside the upper cap combined to the upper portion of the nozzle.

7. The multi-functional cosmetic device of claim 6, wherein a silicon cap is further installed between the upper cap and the upper portion of the nozzle with contacted to the nozzle, in order to reduce noise due to the oscillation of the ultrasonic oscillator and to prevent leaking of liquid other than the spray from the upper end of the nozzle.

8. The multi-functional cosmetic device of claim 7, wherein a lower cap is further installed on the upper portion of the nozzle enclosing the lower portion of the upper cap in order to secure the connection of the upper cap and the upper portion of the nozzle and to prevent leaking of liquid other than the spray from the upper end of the nozzle together with the silicon cap.

9. The multi-functional cosmetic device of claim 1, wherein the solution inlet of the lower end of the nozzle is formed in a structure of a cone with its diameter decreasing from outside to inside.

* * * * *